United States Patent [19]
Marsh et al.

[11] 4,084,093
[45] Apr. 11, 1978

[54] FAN BEAM TRAVERSE-AND-ROTATE CT SCANNER

[75] Inventors: Robin Geoffrey Marsh, Reading; Ian Alexander Fleming, Maidenhead, both of England

[73] Assignee: EMI Limited, Middlesex, England

[21] Appl. No.: 742,708

[22] Filed: Nov. 17, 1976

[30] Foreign Application Priority Data
Dec. 2, 1975 United Kingdom .............. 49347/75

[51] Int. Cl.² ...................... A61B 6/02; G01N 23/08; H05G 1/30
[52] U.S. Cl. ................................. 250/360; 250/445 T
[58] Field of Search .................... 250/445 T, 360, 366

[56] References Cited
U.S. PATENT DOCUMENTS
| | | | |
|---|---|---|---|
| 3,973,128 | 8/1976 | Lemay | 250/445 T |
| 4,010,371 | 3/1977 | Lemay | 250/445 T |

Primary Examiner—Alfred E. Smith
Assistant Examiner—T. N. Grigsby
Attorney, Agent, or Firm—Cooper, Dunham, Clark, Griffin & Moran

[57] ABSTRACT

In a medical radiographic apparatus of the kind in which a fan shaped spread of X-rays is subject to lateral and orbital motions, it is disclosed that the orbital step between each lateral scan need not be exactly related to the angular spread of the fan provided that parallel sets of beams are irradiated over a sufficient number of angles to give a proper evaluation of the absorption of the radiation throughout an examined slice. The orbital step may be larger or smaller than the fan angle and may be variable in the course of the scan if desired.

8 Claims, 4 Drawing Figures

FAN BEAM TRAVERSE-AND-ROTATE CT SCANNER

This invention relates to a method of and apparatus for constructing a representation of the variation of absorption of a planar slice of a body with respect to penetrating radiation such as X- or γ- radiation.

In U.S. Pat. No. 3,778,614, methods of and apparatus for constructing such a representation are described. According to one example described in that specification, a suitable source of radiation provides a pencil beam of radiation and a suitable detector is arranged to provide a measure of the absorption suffered by the beam in passing through the body. The source and detector are each provided with a scanning movement, relative to the body, to provide such a measure of absorption for each of a plurality of substantially parallel pencil beams of radiation at each of a plurality of inclinations in the plane of the slice. Those measurements of absorption are then processed by suitable means to provide a distribution of absorption coefficients for the said slice. To provide the required plurality of beams the source and detector are reciprocated in the plane of the slice and orbited in steps about a common axis normal to that plane.

The processing can be effected, for example in the manner described in the aforementioned specification or in the manner described in U.S. Pat. No. 3,924,129.

In U.S. Pat. No. 3,946,234 there is described a variation of the apparatus of the said U.S. Pat. No. 3,778,614 for the same purpose, in which a source of radiation is arranged to provide a beam of radiation which has a wide angular spread in the plane of the slice. That beam is divided into a plurality of divergent beams by suitable collimators and an array of detectors is provided to measure the intensity of each of those beams after passage through the body. Reciprocating and orbital scanning motions as described hereinbefore are imposed on the source and detectors. As a result of each reciprocating motion, the array of detectors provides absorption information relating to a plurality of sets of parallel beams of radiation, the sets being angularly spaced by the angular separation of the beams of the fan. To provide further sets of beams at different angles the orbital step between each reciprotating movement is then through a step substantially equal to the total angular spread of the fan of radiation. In practice one extreme beam of the fan can be omitted to give an angular spread less than the orbital step by an angle equal to the said angular separation since otherwise certain parallel sets of beam paths would be provided twice, by beams at opposite extremes of the fan. To provide an even angular distribution of such parallel sets of beams over all angles relative to the body the orbital motion continues through nearly 180° since a beam path cannot be significantly distinguished by the direction of travel of the radiation.

According to the invention there is provided an apparatus for examining a slice of a body by means of penetrating radiation including a source of a fan shaped spread of said radiation irradiating the slice, a plurality of detectors, cooperating with respective collimators, to determine the intensity of the radiation transmitted along a plurality of beams within said fan, means for scanning the source and detectors laterally of the slice to provide determinations of the intensity of radiation transmitted along a plurality of sets of parallel paths, each set provided by one of said detectors in the course of the lateral scan and means for orbiting said source and detectors, about a common axis intersecting the slice, through a plurality of angular steps different from the effective angular spread of said fan.

In order that the invention may be clearly understood and readily carried into effect examples thereof will now be described with reference to the accompanying drawings of which:

Figure 1:
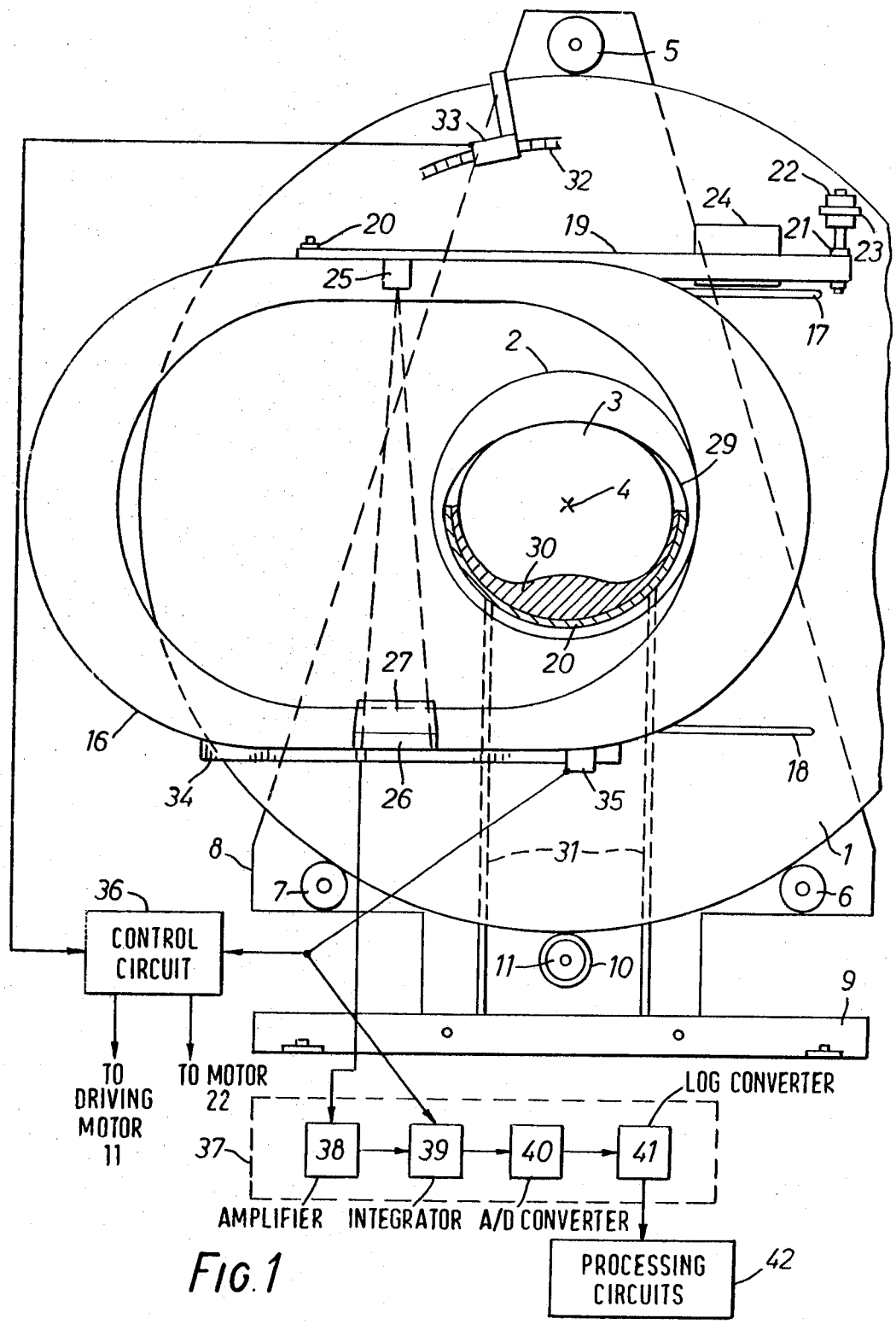
FIG. 1 shows an X-ray apparatus incorporating the invention.

Referring now to FIG. 1, the apparatus shown therein is similar in principle to the apparatus described in the aforementioned U.S. Pat. No. 3,946,234 except in the respects which will be described in greater detail hereinafter. A turntable member 1 having a central aperture 2, to accommodate a body 3 which is to be examined, is mounted vertically for rotation about an axis 4. Axis 4 is disposed centrally in the aperture 2. The member 1 is supported on three rotatable bearings 5, 6 and 7 which are journalled in the main frame 8 of the apparatus. The frame 8 remains atationary, being rigidly secured to a pedestal 9, and can take any suitable form, although it must of course be formed with an aperture coincident with the aperture 2.

The member 1 can be rotated in angular steps, as will be described hereinafter by means of a cog wheel 10 cooperating with gear teeth, not shown, cut into the periphery of the member 1. Cog wheel 10 is driven by a motor 11 which is fixed to main frame 8. If desired the gear teeth may take the form of slots so that the arrangement takes the form of a so called "Geneva mechanism" with cog wheel 10 being replaced by a rotating peg such as is used with that mechanism.

Mounted on the turntable 1, and capable of performing a reciprocating lateral scanning motion relative thereto, is a lightweight but rigid scanning yoke 16. Yoke 16 can run on linear runners 17 and 18 which are fixedly mounted on the rotatable member 1 and are disposed chordally thereof. The lateral scanning motion is imparted to the yoke 16 by virtue of a toothed belt 19, which is stretched between a pair of toothed rollers 20 and 21 journalled in respective brackets, not shown, secured to the member 1. Yoke 16 is attached to belt 19 by means of a bracket, not shown. The roller 20 is merely an idler roller, but roller 21 is driven by a reciprocating motor 22 which is attached by a strap-like bracket 23 to the member 1.

A counter-balance weight 24 is secured to the opposite run, of belt 19, to the yoke 16 and thus moves in opposition thereto to compensate for out-of-balance forces which would otherwise be set up by the lateral scanning motion of the yoke 16 and certain equipment mounted thereon, which will now be described.

Attached to the yoke 16 is a source 25 of penetrating radiation, in this example X-radiation. The radiation is collimated to form a planar, fan-shaped spread of radiation, emanating from an effective point source. On the opposite side of yoke 16, with respect to the aperture 2, to the source 25 is an array 26 of thirty detectors sensitive to the radiation generated by the source 25, each viewing the source through a respective collimator; the collimators being disposed in a bank 27. In this example, neighbouring collimators are inclined to each other at an angle of $\frac{1}{3}°$. Since there are thirty detectors this means that the angular spread of the fan of X-rays generated by the source is 9⅜° between the centre lines of the extreme beams. Since, as mentioned hereinbefore, this is a 10° fan with one exteme beam omitted to prevent duplication if data the fan is not symmetrical about the perpendicular line drawn from the effective point source of the beam of X-radiation to the array 26. This line is in fact arranged to intersect the sixteenth detector in the array 26, in this example, counting from the left in FIG. 1.

The body 3 is supported on a semicylindrical, one part bed 28 and is secured thereon by means of straps such as 29. Gaps between the body and the bed are filled with a suitable packing material 30 which is preferably of dough like consistency and absorbs the X-radiation to substantially the same extent as does human tissue. The material 30 is preferably contained in one or more plastic bags. The bed 28 is supported by legs 31 which stand on the pedestal 9.

As in the aforesaid U.S. Pat. No. 3,946,234 the rotational scanning motion, imparted by the cog wheel 10 to the member 1, needs to be synchronised with the lateral scanning motion imparted to the yoke 16 by the reciprocating motor 22. To this end the member 1 is formed with an annular graticule, part of which is shown at 32, and a fixed photodetector 33 which with a light source, not shown, is mounted on main frame 8. Photodetector 33 provides timing pulses indicative of the passage of markings on the graticule 32 past the photodetector 33. Thus the rotational scanning motion of member 1 is monitored. Similarly a linear graticule 34 is fixedly attached to the yoke 16 and cooperates with a second photodetector 35, which is mounted on the member 1 so as to rotate therewith, and a similarly mounted light source, not shown, to produce timing pulses indicative of the progress of the lateral scanning. Both graticules 32 and 34 comprise translucent or transparent members bearing opaque lines printed, etched or otherwise provided thereon. The two sets of timing pulses are fed to a control circuit 36 which controls the motor 22 and the motor 11 in such a way that, after each step of rotational motion, a single lateral scan is carried out to traverse the source 25 and the detector array 26 in one direction or the other across the aperture 2. Thus a single lateral scan is carried out for each dwell angle of the member 1.

Each detector in the array 26 comprises, for example a scintillator crystal, such as sodium iodide, and an associated photomultiplier tube, or a photodiode, and thus provides electrical signals indicative of the amount of radiation detected thereby. The electrical signals so provided are applied to respective pre-processing circuits 37, each of which contains an amplifier 38, a resettable integrator 39, an analogue-to-digital converter 40 and a logarithmic converter 41. The integrators 39 are read and reset synchronously and periodically by means of timing pulses derived from the photodetector 35; the arrangement in this example being such that the reading and re-setting occurs some one hundred and sixty times during each lateral scan in either direction. Thus, during a single lateral scan, output signals are provided which are indicative of the absorption suffered by the X-radiation on traversing a set of one hundred and sixty parallel paths from the source to the detector at each of thirty angular orientations with respect to the body 3. The member 1 is then rotated through a predetermined angle and a second group of thirty sets of one hundred and sixty output signals are derived. The process is repeated until such sets have been provided over about 180° and all of the output signals obtained during the scanning are processed in a processing circuit 42 to evaluate the absorption coefficient, with respect to the radiation used, at a plurality of locations distributed over the slice of the body 3 which lies in the plane of the beam of X-rays generated by the source 25.

Preferably the processing is carried out in accordance with the technique described in U.S. Pat. No. 3,924,129. As previously mentioned this technique involves a form of convolution and the output signals are assembled in sets relating to parallel paths through the body. Each output signal is then modified by combining it with weighted components of other output signals of its own set; the weighting being in accordance with a function which is negative, and decreases in amplitude as the distance from the path giving rise to the output signal being modified increases. The modified output signals are then additively combined in accordance with a layergramming procedure; the modification of the output signals being such as to compensate for the known inaccuracies of conventional layergrams. In relation to a predetermined point in the slice being examined the arrangement is such that the modified absorption values for all beam paths passing through, or near to, that point are combined to give an absorption coefficient for the point. In practice beams at the angular dispositions of all of the parallel sets of paths may not pass sufficiently close to each such evaluation point. For this reason interpolation is applied to the modified data for each parallel set of paths to obtain modified data for a new set of an increased number of such paths to ensure that at least one passes sufficiently close to each evaluation point.

Figure 2:
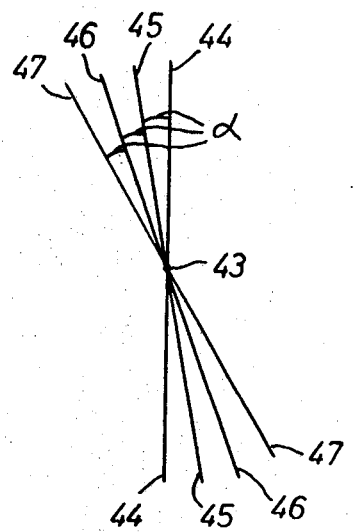
FIGS. 2, 3 and 4 are diagrams used to explain the invention.

As mentioned hereinbefore, the arrangement of the said U.S. Pat. No. 3,946,234 was such that the orbital step was substantially equal to the orbital fan angle. Thus the angular distribution of beam paths was completed at substantially even spacing in the course of nearly 180° rotation. The situation is illustrated in FIG. 2 for beams through a typical evaluation point 43 in the slice. Assuming the total fan angle to be nearly $\alpha$ degrees from beam centreline to beam centreline, usually 9⅜° where $\alpha$ is 10°, one lateral scan will provide through each point such as 43 data for beam paths between limits 44 and 45, as a result of the angular distribution of beams within the fan. It will be understood that the individual data will not be provided by the same detector or at one time and that they may also be interpolated values or may not pass exactly through point 43.

An orbital step of $\alpha$ degrees now takes place so that a further lateral scan provides data for beam paths between limits 45 and 46 and a further step gives data between limits 46 and 47 and so on.

It will be seen that each beam passes through regions to two sides of point 43 so that $m-1$ angular steps, where $m\alpha = 180°$ are sufficient to provide equally angularly spaced beams passing through or close to point 43 over a complete spread of 360°.

In the specification of the said U.S. Pat. No. 3,946,234 it is considered that the beams passing through each evaluation point and therefore the successive parallel sets of paths, should be substantially evenly distributed in angle. However it is not necessary for all possible forms of processing that this should be so. In the case of the convolution processing referred to hereinbefore it is desirable that they should be evenly angularly distributed but in practice deviation from such distribution can be tolerated without excessive error if other gains can be made from such a relationship.

Figure 3:
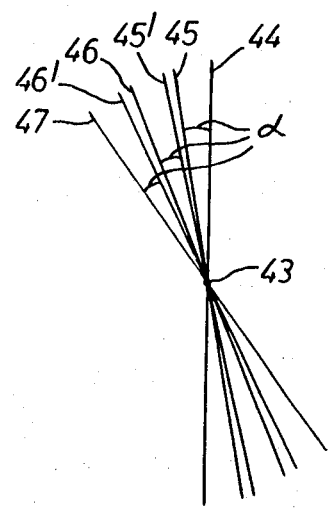

In the arrangement of this invention the motor 11 operates in conjunction with the control circuit 36 to provide an orbital step, between successive lateral scans, which is not directly related to the angle $\alpha$ subtended by the fan of radiation at the source 25. For the purposes of defining a direct relationship it is considered herein that a spread of radiation of angle equal to the orbital step less the beam spacing angle is effectively equivalent to a spread equal to the orbital step since both produce an even angular spacing of examined paths, for the reasons explained hereinbefore. However larger deviations from the orbital step angle, sufficient to produce irregular angular spacing of the examined paths, are considered to fall within this invention. In a preferred example the orbital step is arranged to be eleven degrees compared with the fan angle $\alpha$ of 10°. The significance of this is illustrated in FIG. 3, which is drawn with exaggerated differences in angle for the sake of clarity. As before, the first lateral scan provides data for beam paths distributed in angle between limits 44 and 45. However in this example the orbital step is through an angle significatnly larger that $\alpha°$ so that the beam paths for the second and third lateral scans lie between limits 45' and 46 and 46' and 47 etc. Of course no data is provided for the sectors between 45 and 45' and 46 and 46' but the error is not excessive. These blank sectors may be as large as is found in practice not to give excessive errors.

The sectors for which data is provided need not be examined over a single 180° of orbit but can be filled in over a larger angle of orbit if desired.

Figure 4:
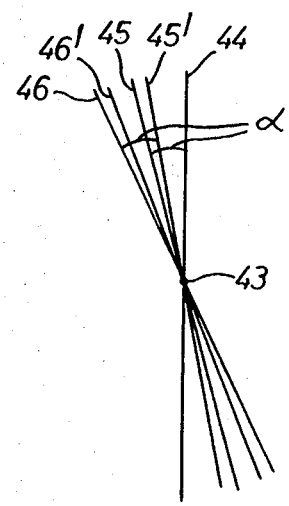

Alternatively the orbital step can be smaller than $\alpha°$, say 8.5°, as is shown in FIG. 4 which is also out of scale. In that example the first lateral scan provides the data for paths distributed in angle between limits 44 and 45 as before. However the orbital step is such that the next lateral scan provides data for paths between 45' and 46. It will be seen that some overlap is provided in the regions between 45' and 45, 46' and 46 and so on. Since the orbital step does not relate in any exact significant relationship to the fan angle the overlapping beam paths in regions such as 45 to 45' will not exactly overlie each other. The effect is then to provide a slightly greater density of paths in those regions. Duplicated data can be omitted or averaged if desired.

The same effect as that of FIG. 4 may be achieved with the FIG. 3 arrangement if the gaps left by the increased orbital step are overlaid by evaluated regions in the course of an extension of the orbit beyond 180°. In that case, provided the gaps have an angular extent less than the fan angle, i.e. the orbital steps is less than twice the fan angle, a certain degree of overlap will be provided during the extended orbit.

Other relationships may readily be devised in accordance with the invention. It is important to ensure that there is a reasonable angular distribution of beam paths through points such as 43 over a full 360°, in either direction, but the distribution of such paths need not be exactly regular.

As mentioned hereinbefore the actually measured beam paths may not pass sufficiently close to the evaluation points so that interpolation is required. By using the invention it may be convenient to adjust the orbital step to cause the actual beams to pass as close as possible to the evaluation points for the purpose of reducing interpolation requirements. It is not, of course, necessary, but is rather convenient, that the orbital step is of constant value throughout the total orbital angle.

Additional refinements may be made to the apparatus shown in FIG. 1 without departing from the scope of the invention. For example blocks of X-ray absorbent material could be disposed between the source 25 and the body 3 and between the body 3 and the detector array 26 to tend to reduce variations in the degree of absorption suffered by the radiation on traversing paths of different lengths through the body 3. Moreover the blocks may be arranged to impart a specified attenuation to the radiation when it traverses paths wholly outside the body 3 and its supporting bed so as to permit the sensitivities of the various detectors to be monitored. In this regard it is advantageous to use the technique, disclosed in the aforementioned U.S. Pat. No. 3,946,234 in which reference readings for the detectors in one half of the fan-shaped beam of radiation are obtained at one side of the aperture 2 whilst those for detectors in the other half of the beam are obtained at the other side of the aperture 2.

In some circumstances, it can be difficult to physically accommodate the large number of detectors used in side-by-side relationship in the array 26 and in such cases it is desirable to stagger the detectors in distance from the source. The stagger should, of course, be kept to a minimum.

What we claim is:

1. An apparatus for examining a slice of a body by means of penetrating radiation including a source of a fan shaped spread of said radiation irradiating the slice, a plurality of detectors, cooperating with respective collimators, to determine the intensity of the radiation transmitted along a plurality of beams within said fan, means for scanning the source and detectors laterally of the slice to provide determinations of the intensity of radiation transmitted along a plurality of sets of parallel paths, each set provided by one of said detectors in the course of the lateral scan and means for orbiting said source and detectors, about a common axis intersecting the slice, through a plurality of angular steps different from the effective angular spread of said fan.

2. An apparatus according to claim 1 in which each of the said angular steps is greater that the said effective angular spread.

3. An apparatus according to claim 2 in which each of the said angular steps is less than twice the said effective angular spread.

4. An apparatus according to claim 1 in which all of the said angular steps are substantially equal.

5. An apparatus according to claim 1 in which the total orbital motion extends over an angle greater than 180°.

6. An apparatus according to claim 1 including means for processing the said determination of intensity to provide estimates of the absorption of the radiation in elements of a matrix of notional elements delineated in the said slice.

7. An apparatus according to claim 6 in which the said angular steps are chosen to provide the said parallel paths at predetermined positions in relation to said elements.

8. An apparatus for examining a slice of a body by means of penetrating radiation including a source of a fan shaped spread of said radiation irradiating the slice, a plurality of detectors, cooperating with respective collimators, to determine the intensity of the radiation transmitted along a plurality of equi-angularly spaced beams within said fan, means for scanning the source and detectors laterally of the slice to provide determinations of the intensity of radiation transmitted along a plurality of sets of parallel paths, each set provided by one of said detectors in the course of the lateral scan and means for orbiting said source and detectors, about a common axis intersecting the slice, to provide further pluralities of said sets at different angular dispositions in said slice such that the overall angular distribution of said sets in said slice is not uniform.

* * * * *